United States Patent
Sato et al.

[11] Patent Number: 5,914,419
[45] Date of Patent: Jun. 22, 1999

[54] ORGANOSILICON COMPOUND

[75] Inventors: Shinichi Sato; Noriyuki Koike; Masatoshi Arai, all of Gunma-Ken, Japan

[73] Assignee: Shin-Etsu Chemical Co., Ltd., Tokyo, Japan

[21] Appl. No.: 08/908,937

[22] Filed: Aug. 8, 1997

[30] Foreign Application Priority Data

Aug. 9, 1996 [JP] Japan ................................. 8-227879

[51] Int. Cl.⁶ ....................................................... C07F 7/10
[52] U.S. Cl. ................................................................ 556/410
[58] Field of Search ................................................ 556/410

[56] References Cited

U.S. PATENT DOCUMENTS

| | | | |
|---|---|---|---|
| 3,576,021 | 4/1971 | Grindahl | 556/410 |
| 4,469,881 | 9/1984 | Arkles | 556/410 X |
| 5,082,962 | 1/1992 | Schilling | 556/410 X |
| 5,486,633 | 1/1996 | Pirrung et al. | 556/410 |

FOREIGN PATENT DOCUMENTS

| | | |
|---|---|---|
| 0 488 681 | 6/1992 | European Pat. Off. . |
| 0 563 811 | 10/1993 | European Pat. Off. . |

OTHER PUBLICATIONS

Chem. Abstracts., vol. 114, No. 11, Mar. 18, 1991, Abstract No. 100651d.

*Primary Examiner*—Paul F. Shaver
*Attorney, Agent, or Firm*—Millen, White, Zelano, & Branigan, P.C.

[57] ABSTRACT

The organosilicon compound of the following chemical formula, which is useful for introduction of silylphenyl groups having a hydrosilyl group into polymer terminals and the like, is disclosed.

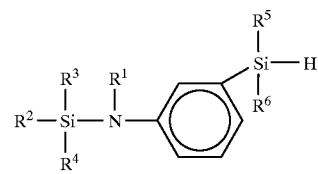

wherein $R^1$ is a hydrogen atom or a substituted or unsubstituted monovalent hydrocarbon group; $R^2$, $R^3$, $R^4$, $R^5$ and $R^6$ are each a hydrogen atom or a substituted or unsubstituted monovalent hydrocarbon group.

7 Claims, 1 Drawing Sheet

ORGANOSILICON COMPOUND

FIELD OF THE INVENTION

The present invention relates to a novel organosilicon compound undisclosed in literatures and, more particularly, to an organosilicon compound which is useful for as raw materials to introduce silylphenyl groups having a hydrosilyl group into polymer terminals and the like.

BACKGROUND OF THE INVENTION

A carbon-functional silane is useful for as coupling agents, crosslinking agents of organic polymers or functional surface treating agents. The organogroups of the carbon functional-silane are each bonded to a silicon atom via carbon chain. As for a process for forming this carbon to silicon bond, a hydrosilylation reaction, which has little by-product and also is whose reaction is easy so that which is adequate for industrial mass production, is important.

Accordingly, up to this time, introducing a hydrosilyl group into polymer terminals or the like has been widely put into practice, but a hydrosilylation agent appropriate for introducing silylphenyl groups having a hydrosilyl group has not been known yet.

SUMMARY OF THE INVENTION

Therefore, an object of the present invention is to provide an organosilicon compound which is useful for as raw materials to introduce silylphenyl groups having a hydrosilyl group into polymer terminals or the like.

The above object of the present invention is attained by an organosilicon compound represented by the following chemical formula.

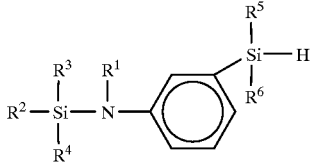

wherein $R^1$ is a hydrogen atom, or a substituted or unsubstituted monovalent hydrocarbon group; $R^2$, $R^3$, $R^4$, $R^5$ and $R^6$ are each a hydrogen atom, or a substituted or unsubstituted monovalent hydrocarbon group.

DETAILED DESCRIPTION OF THE INVENTION

Figure 1:
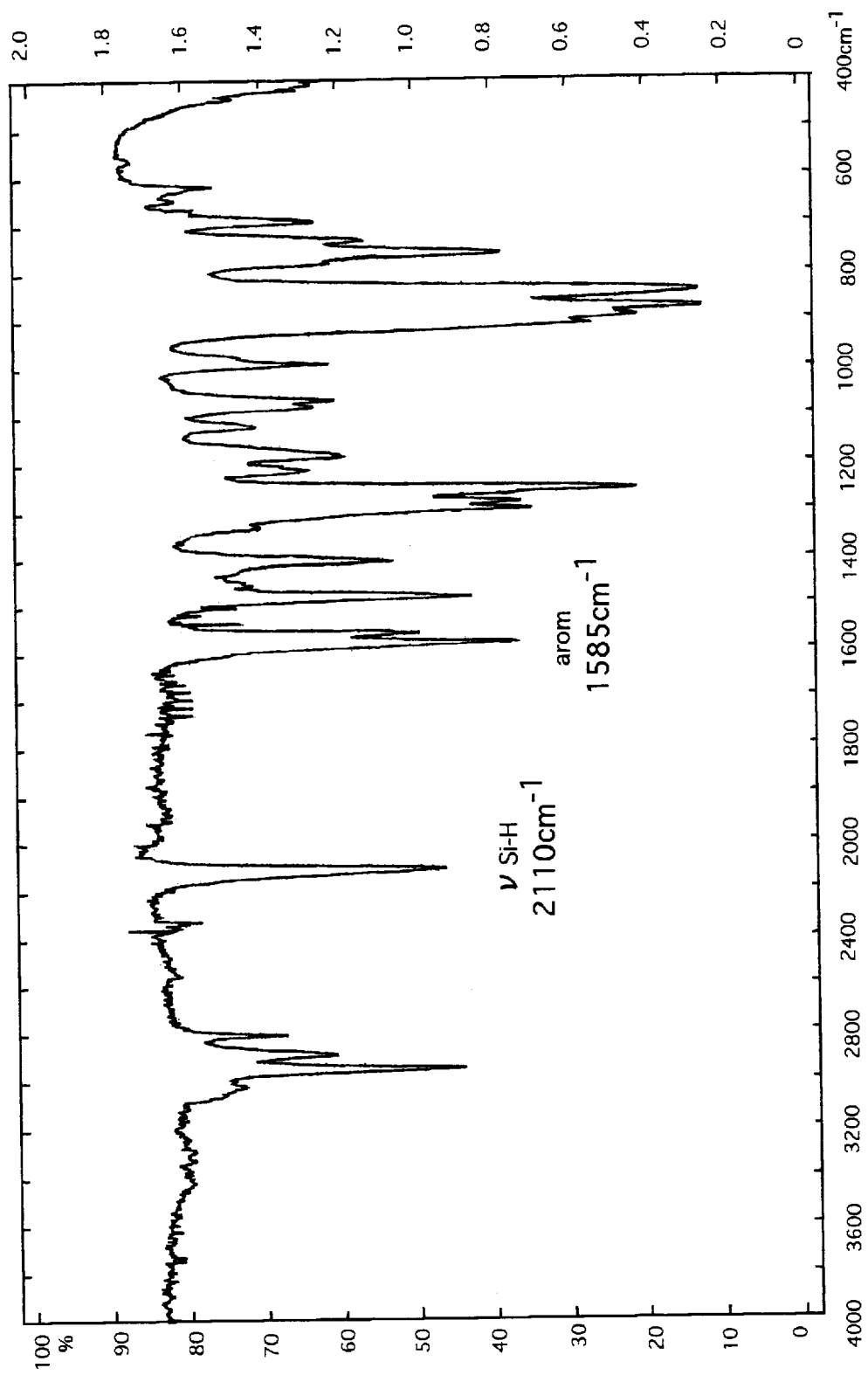
FIG. 1 is the IR spectrum of the organosilicon compound of the present invention obtained in the Example 1.

Exemplary a substituted or unsubstituted monovalent hydrocarbon group of $R^1$, $R^2$, $R^3$, $R^4$, $R^5$ and $R^6$ in the organosilicon compound of the present invention expressed by the chemical formula

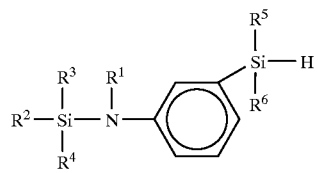

includes alkyl groups such as methyl, ethyl, propyl, and the like; cycloalkyl groups such as cyclohexyl, and the like; alkenyl groups such as vinyl, allyl, and the like; aryl groups such as phenyl, tolyl, and the like; and otherwise these groups whose hydrogen atoms are partially substituted by halogen atoms and the like.

The organosilicon compounds of the present invention will be exemplified below, but these copounds are representative examples, and accordingly, the organosilicon compounds of the present invention are not limited to these compounds. Hereinafter, "methyl" is abbreviated as "Me", and "phenyl" is abbreviated as "Ph".

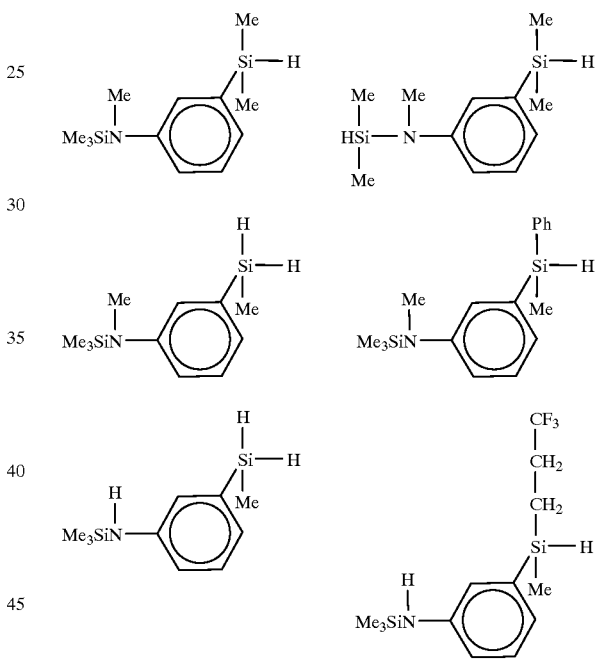

The organosilicon compounds of the present invention can be synthesized by, for example, reacting the silylmetahaloaniline derivative of the following formula with magnesium to prepare a Grignard reagent and then reacting it with a hydroorganochlorosilane.

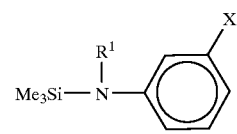

wherein X is a halogen atom; $R^1$ is a hydrogen atom or a substituted or unsubstituted monovalent hydrocarbon group.

In above reaction, an ether group solvent such as THF, and the like is necessary to be used as a solvent. A reaction temperature is preferable to be in the range of from 40 to 70° C.

A compound of the present invention is useful for as an intermediate for introducing a reactive silyl group into polymer terminals. A polymer, having the compound of the present invention in it's terminal, can form a cured product by the hydrosilylation reaction with a compound having a vinyl group under the existence of a platinum catalyst. This cured product, depending on the molecular weight of the polymer, may be in the form of resin, elastomer, gel or the like. These cured products are useful for adhesive agent, gel, sealing material, coating material, releasing agent and the like.

The present invention will now be illustrated in more detail by reference to the following examples, but these examples do not limit the scope of the invention. It should be understood that all modifications falling the true spirit and scope of the present invention are intended to be covered by the appended claims.

EXAMPLE 1

Into a 500 ml four neck distillation flask equipped with stirring rod, thermometer, Dimroth and dropping funnel, 5.7 g of magnesium powder, 100 g of tetrahydrofuran and 0.02 g of iodine were poured, and then 46.0 g of the silyl-metachloroaniline shown below was dropped at 60° C. for 24 hours by using the dropping funnel to prepare a Grignard reagent.

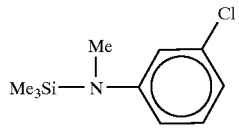

After cooling down to a room temperature, 24.4 g of dimethylchlorosilane was dropped from the dropping funnel. After maturing at 60° C. for 2 hours, the produced magnesium salt was filtered, and the filtered solution was distilled to obtain 13.1 g of a fraction having boiling point of 75 to 76° C./2 mmHg and reflactive index of 1.5103 (25° C.). This fraction was analized by applying $^1$H-NMR, IR and elemental analysis to confirm the compound represented by the following chemical formula.

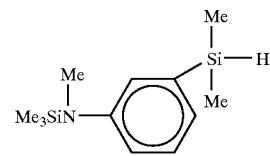

$^1$H-NMR: δ0.25 (s, N—Si—CH$_3$, 9H), δ0.35 (s, C—Si—CH$_3$, 6H), δ2.85 (s, N—CH$_3$, 3H), δ4.31 (m, Si—H, 1H), δ6.5 to 7.1 (m, arom., 4H).

IR (cf. FIG. 1): 1585 cm$^{-1}$ arom., 2110 cm$^{-1}$ $v_{Si-H}$.

| Elemental Analysis: | C | H | N | Si |
|---|---|---|---|---|
| Measured Value | 60.69% | 9.76% | 5.90% | 23.65% |
| Calculated Value | 60.65% | 9.71% | 5.85% | 23.70% |

What is claimed is:

1. An organosilicon compound represented by the following chemical formula;

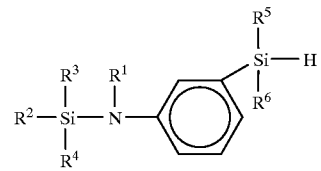

wherein R$^1$ is a hydrogen atom or a substituted or unsubstituted monovalent hydrocarbon group; R$^2$, R$^3$, R$^4$, R$^5$ and R$^6$ are each a hydrogen atom or a substituted or unsubstituted monovalent hydrocarbon group.

2. An organosilicon compound as defined in claim 1, wherein R$^2$, R$^3$, and R$^4$ are one groups selected from alkyl groups.

3. An organosilicon compound as defined in claim 2, wherein R$^2$, R$^3$ and R$^4$ are methyl groups, respectively.

4. An organosilicon compound as defined in claim 1, wherein R$^1$ is methyl group.

5. An organosilicon compound as defined in claim 1, wherein R$^1$ is hydrogen atom.

6. An organosilicon compound as defined in claim 4 wherein R$^2$, R$^3$ and R$^4$ are methyl groups, respectively.

7. An organosilicon compound as defined in claim 5 wherein R$^2$, R$^3$ and R$^4$ are methyl groups, respectively.

* * * * *